(12) United States Patent
Srinivasan et al.

(10) Patent No.: US 7,015,306 B2
(45) Date of Patent: Mar. 21, 2006

(54) LABELED NEUROTENSIN DERIVATIVES

(75) Inventors: Ananthachari Srinivasan, St. Charles, MO (US); Jack L. Erion, St. Charles, MO (US); Michelle A. Schmidt, Belleville, IL (US)

(73) Assignee: BioSynthema, Inc., St. Louis, MO (US)

( * ) Notice: Subject to any disclaimer, the term of this patent is extended or adjusted under 35 U.S.C. 154(b) by 265 days.

(21) Appl. No.: 10/036,918

(22) Filed: Dec. 21, 2001

(65) Prior Publication Data

US 2005/0191240 A1    Sep. 1, 2005

Related U.S. Application Data

(63) Continuation of application No. PCT/US00/17509, filed on Jun. 22, 2000.

(60) Provisional application No. 60/213,068, filed on Jun. 21, 2000, provisional application No. 60/140,913, filed on Jun. 24, 1999.

(51) Int. Cl.
 *C07K 17/00* (2006.01)
 *A61K 38/00* (2006.01)
 *G01N 33/574* (2006.01)

(52) U.S. Cl. ............... 530/329; 530/323; 530/327; 514/14; 514/16; 514/17; 424/1.11; 424/1.57; 424/1.69; 424/9.1; 435/7.23; 435/7.75

(58) Field of Classification Search ............ 530/329, 530/323, 327; 514/14, 16, 17; 424/1.11, 424/1.57, 1.69, 9.1; 435/7.23, 7.75
See application file for complete search history.

(56) References Cited

FOREIGN PATENT DOCUMENTS

EP       0606804 A       7/1994
WO       WO 95/22341     8/1995

OTHER PUBLICATIONS

Visser et al., Eur. J. Nucl. Med. Mol. Imaging, vol. 30, No. 8, pp. 1134-1139, Aug. 2003.*
Achilefu et al., J. Med. Chem., vol. 46, No. 15, pp. 3403-3411, 2003.*
Chavatte, K.; Wong, E.; Fauconnier, T.K.; Lu, L.; Nguyen, T.; Roe, D.; Pollack, A.; Eshima, D.; Terriere, D.; Mertens, J.; Iterbeke, K., Tourwe, D.; Thornback, J.; Bossuyt, A.; Rhenium (Re) and Technetium (Tc)-99m Oxocomplexes of Neurotensin (8-13), 6001, vol. 131, Chemical Abstracts (Abstract No. 99344y), No. 8; 1999; Columbus, Ohio, USA.
Chavatte, K.; Wong, E.; Fauconnier, T.K.; Lu, L.; Nguyen, T.; Roe, D.; Pollack, A.; Eshima, D.; Terriere, D.; Mertens, J.; Iterbeke, K., Tourwe, D.; Thornback, J.; Bossuyt, A.; Rhenium (Re) and Technetium (Tc)-99m Oxocomplexes of Neurotensin (8-13), Journal of Labelled Compounds and Radiopharmaceuticals, Abstract, vol. 42, No. 5, pp. 415-421; 1999; John Wiley & Sons, Ltd., USA.

* cited by examiner

*Primary Examiner*—Jon Weber
*Assistant Examiner*—Abdel A. Mohamed
(74) *Attorney, Agent, or Firm*—Blackwell Sanders Peper Martin LLP

(57) ABSTRACT

Peptide analogs of neurotensin are disclosed which are resistant to enzymatic degradation and which retain high binding affinity for neurotensin receptors. Pharmaceutical compositions of these compounds are useful for diagnostic and therapeutic purposes.

14 Claims, No Drawings

SEQUENCE LISTING

<160> NUMBER OF SEQ ID NOS: 6

<210> SEQ ID NO 1
<211> LENGTH: 13
<212> TYPE: PRT
<213> ORGANISM: Artificial Sequence
<220> FEATURE:
<223> OTHER INFORMATION: Derived from Homo sapiens
<220> FEATURE:
<221> NAME/KEY: MOD_RES
<222> LOCATION: (1)
<223> OTHER INFORMATION: Pyroglutamic acid.

<400> SEQUENCE: 1

Xaa Leu Tyr Glu Asn Lys Pro Arg Arg Pro Tyr Ile Leu
 1               5                  10

<210> SEQ ID NO 2
<211> LENGTH: 6
<212> TYPE: PRT
<213> ORGANISM: Artificial Sequence
<220> FEATURE:
<221> NAME/KEY: MOD_RES
<222> LOCATION: (1)
<223> OTHER INFORMATION: Diethylenetriamine pentaacetic acid (DTPA) is
       coupled to this residue.
<220> FEATURE:
<221> NAME/KEY: MOD_RES
<222> LOCATION: (1)..(2)
<223> OTHER INFORMATION: These two residues are joined by a pseudo
       peptide bond.
<220> FEATURE:
<223> OTHER INFORMATION: Description of Artificial Sequence:Synthetic
       peptide with a pseudopeptide bond.

<400> SEQUENCE: 2

```
Lys Arg Pro Tyr Ile Leu
 1               5
```

<210> SEQ ID NO 3
<211> LENGTH: 6
<212> TYPE: PRT
<213> ORGANISM: Artificial Sequence
<220> FEATURE:
<221> NAME/KEY: MOD_RES
<222> LOCATION: (1)
<223> OTHER INFORMATION: Diethylenetriamine pentaacetic acid (DTPA) is
      coupled to this residue.
<220> FEATURE:
<223> OTHER INFORMATION: Description of Artificial Sequence:Synthetic
      peptide.

<400> SEQUENCE: 3

```
Arg Arg Pro Tyr Ile Leu
 1               5
```

<210> SEQ ID NO 4
<211> LENGTH: 8
<212> TYPE: PRT
<213> ORGANISM: Artificial Sequence
<220> FEATURE:
<221> NAME/KEY: MOD_RES
<222> LOCATION: (1)
<223> OTHER INFORMATION: Diethylenetriamine pentaacetic acid (DTPA) is
      coupled to this residue.
<220> FEATURE:
<221> NAME/KEY: MOD_RES
<222> LOCATION: (1)
<223> OTHER INFORMATION: This residue is piperidinylglycine.
<220> FEATURE:
<221> NAME/KEY: MOD_RES
<222> LOCATION: (3)
<223> OTHER INFORMATION: This residue is (N-amidinopiperidinyl) glycine.
<220> FEATURE:
<221> NAME/KEY: MOD_RES
<222> LOCATION: (7)
<223> OTHER INFORMATION: This residue is t-butylglycine.
<220> FEATURE:
<223> OTHER INFORMATION: Description of Artificial Sequence:Synthetic
      peptide.

<400> SEQUENCE: 4

```
Xaa Pro Xaa Arg Pro Tyr Xaa Leu
 1               5
```

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence:Synthetic
      peptide.
<220> FEATURE:
<221> NAME/KEY: MOD_RES
<222> LOCATION: (1)
<223> OTHER INFORMATION: Diethylenetriamine pentaacetic acid (DTPA) is
      coupled to this residue.
<220> FEATURE:
<221> NAME/KEY: MOD_RES
<222> LOCATION: (1)
<223> OTHER INFORMATION: This residue is trans-(4-aminomethyl)
      cyclohexylalanine.
<220> FEATURE:
<221> NAME/KEY: MOD_RES
<222> LOCATION: (3)
<223> OTHER INFORMATION: This residue is (N-amidinopiperidinyl) glycine.
<220> FEATURE:
<221> NAME/KEY: MOD_RES
<222> LOCATION: (7)
<223> OTHER INFORMATION: This residue is t-butylglycine.

```
<400> SEQUENCE: 5

Xaa Pro Xaa Arg Pro Tyr Xaa Leu
 1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence:Synthetic
      peptide.
<220> FEATURE:
<221> NAME/KEY: MOD_RES
<222> LOCATION: (1)
<223> OTHER INFORMATION: Diethylenetriamine pentaacetic acid (DTPA) is
      coupled to this residue.
<220> FEATURE:
<221> NAME/KEY: MOD_RES
<222> LOCATION: (1)
<223> OTHER INFORMATION: This residue is piperidinylalanine.
<220> FEATURE:
<221> NAME/KEY: MOD_RES
<222> LOCATION: (3)
<223> OTHER INFORMATION: This residue is (N-amidinopiperidinyl) glycine.
<220> FEATURE:
<221> NAME/KEY: MOD_RES
<222> LOCATION: (7)
<223> OTHER INFORMATION: This residue is t-butylglycine.

<400> SEQUENCE: 6

Xaa Pro Xaa Arg Pro Tyr Xaa Leu
 1               5
```

LABELED NEUROTENSIN DERIVATIVES

APPLICATION CROSS-REFERENCE

This application claims priority to and is a continuation of International Application No. PCT/US00/17509, filed Jun. 22, 2000. This application also claims priority of U.S. Provisional Application No. 60/140,913, filed Jun. 24, 1999 and U.S. Provisional Application No. 60/213,068, filed Jun. 21, 2000.

FIELD OF THE INVENTION

The present invention relates to: labeled peptide compounds, a method of preparing the compounds such that they are resistant to enzymatic degradation, a pharmaceutical composition comprising these compounds, and use of these compounds for the purposes of diagnosis and therapy.

BACKGROUND OF THE INVENTION

Neurotensin (NT) is a thirteen amino acid peptide, isolated from bovine hypothalamus and has the following structure: pGlu-Leu-Tyr-Glu-Asn-Lys-Pro-Arg-Arg-Pro-Tyr-Ile-Leu-OH (SEQ ID NO:1) wherein pGlu is pyroglutamate. High concentrations of neurotensin receptors are found in discrete regions of the mammalian central nervous system including the brain and in the gut. In addition, neurotensin receptors are found in several tumor cells, including small cell lung carcinoma, exocrine pancreatic cancer (Reubi et al., 1998), Ewing sarcoma, meningiomas, medulloblastomas and astrocytomas. Normal pancreatic tissue and tissue from patients with pancreatitis or endocrine pancreatic cancer do not express neurotensin receptors (Reubi et al., 1998). It is estimated that there are 58,000 cases of exocrine pancreatic cancer per year in the United States and Europe. The five year survival rate for patients with exocrine pancreatic cancer is low, in the range of 5–10%. Current diagnosis for this cancer uses a combination of radiologic procedures and biopsies. An early diagnostic method coupled with a therapeutic counterpart may have a profound effect on survival and quality of life.

Structure-activity relationships have shown that the C-terminal sequence (amino acid residues 8–13 (named NT(8–13))) of the natural neurotensin is sufficient for preserving high affinity receptor binding (Granier et al., 1982; Kitabgi et al., 1985). The affinity of this analog is comparable to that of natural neurotensin in two different binding assays, i.e., the binding assay on rat brain synaptic membranes and on HT 29 cells which express neurotensin receptors. Unfortunately this truncated peptide has poor in vitro stability. One site of enzymatic instability is the $Arg^8$-$Arg^9$ bond which has a serum $t_2$ of 5 minutes. The serum stability was increased with the $Lys^8(\Psi\text{-}CH_2NH)Arg^9$ pseudo-peptide DTPA-$Lys^8(\Psi\text{-}CH_2NH)Arg^9$-Pro-Tyr-Ile-Leu-OH (SEQ ID NO:2) (Tourwe et al., 1998).

Two radioiodinated derivatives of neurotensin are described in the literature. Because there are two tyrosine residues, iodination yields a complex mixture of products. These derivatives are difficult to purify and each one possesses different biological properties. To overcome this problem, Mazella et al. (1983) synthesized monoiodo-125-[$Trp^{11}$]-neurotensin. This derivative has a $K_d$ of 0.1 nM binding to rat brain synaptic membranes. The same group of researchers later succeeded in preparing the monoiodo-125 derivative of natural neurotensin derivative. This radioiodo analog has a $K_d$ of 0.26 nM for binding on human brain neurotensin membranes.

These iodinated derivatives of natural neurotensin peptides are unsuitable for imaging and therapy of tumors expressing neurotensin receptors because of difficulty in the method of preparation as well as the instability of these derivatives. The instability results from rapid deiodination and also from the enzymatic degradation of the natural neurotensin peptide bonds.

NT(8–13) contains only one Tyr residue which can be selectively radioiodinated. Structure activity studies indicated that the iodination resulted in the loss of binding affinity by a factor of 20.

Since the early work, other radiolabeled neurotensin analogs have been prepared. Tourwe et al. (1998) have prepared diethylenetriamine pentaacetic acid (DTPA)-NT(8–13) (DTPA-Arg-Arg-Pro-Tyr-Ile-Leu-OH (SEQ ID NO:3)) and found that the derivative had an affinity of 6.5 nM to HT 29 colon adenocarcinoma cells. The low tumor uptake in nude mice HT29 tumor was ascribed to the rapid metabolism of the DTPA-NT(8–13). The in vivo half-life of neurotensin is less than 1.5 minutes and the major cleavage site has been shown to be the $Arg^8$-$Arg^9$ bond (Lee et al., 1984; Aronin et al., 1982). Hence, neurotensin analogs in which the peptide bonds were sequentially replaced by $\Psi(CH_2NH)$ were prepared and a large drop in affinity was observed. The compounds DTPA-$Lys^8$-$\Psi(CH_2NH)$-$Arg^8$-NT(8–13) and DTPA-$Lys^8$-$\Psi(CH_2NH)$-$Lys^8$-NT(8–13) had a $K_d$ of 13 and 7.4 nM, respectively.

An analysis of the above compounds indicated that the stability of the compounds in the serum is not sufficient for these compounds to be used as radiolabeled imaging and therapeutic agents.

The publications and other materials used herein to illuminate the background of the invention or provide additional details respecting the practice, are incorporated by reference, and for convenience are respectively grouped in the appended List of References.

SUMMARY OF THE INVENTION

Neurotensin analogs containing Arg mimics have been synthesized. Studies demonstrate that replacement of $Arg^8$ does not significantly affect the binding affinity and replacement of $Arg^9$ is not tolerated. The best results are obtained by replacing $Arg^8$ with (4-Gu)Phe or Gly(PipAm) ((N-amidinopiperidinyl)glycine) as the arginine surrogate. The $IC_{50}$ values for these two peptides are comparable to native neurotensin. While serum stability is improved by the incorporation of Arg mimics, optimum stability is not achieved by that change alone. Another source of instability is the C-terminus with the Ile-Leu-OH being metabolized. Replacement of the C-terminus with a bulkier side chain stabilized the bond from degradation. Replacement of Ile with tBuGly results in no loss of binding affinity, although the presence of the pseudo-peptide bond or the C-terminal amide abolishes receptor affinity. Neurotensin analogs are described which are useful for diagnostic and therapeutic purposes.

DETAILED DESCRIPTION OF THE INVENTION

Neurotensin has a short half-life in vivo thereby limiting its usefulness as a diagnostic or therapeutic agent. It is desirable to have a compound with a stability such that 70–80% of the injected compound is present in the subject=s serum and urine at the end of 4 hours after administration. Several neurotensin analogs have been synthesized, as disclosed herein, which are stable and still show strong binding affinity to neurotensin receptors.

The phrase "spacer unit" as used herein designates any combination of amino acids or amino acid residues, a combination of amino acids or amino acid residues with a non-amino acid moiety, or any non-amino acid moiety which removes (i.e., spaces) a chelating moiety from a binding portion of a peptide.

The phrase "selective affinity" as used herein means a binding affinity at least in the micromolar or stronger binding. Selective affinity includes a $K_d$ in the micromolar, nanomolar or stronger range.

The initial changes made to neurotensin consisted of replacing the arginine at amino acid position 1 of NT(8–13) with an arginine mimic. It was further recognized that there is a secondary site of metabolism between Ile-Leu-OH ($AA_5$-$AA_6$). Hence Ile was replaced by a bulkier side chain to stabilize the bond from further degradation. The combination of both modifications is essential for the stabilization of natural neurotensin derivatives as well as its analogs. Other modifications such as replacement of Arg-9-neurotensin ($AA_2$) results in the loss of binding affinity.

The present invention is further detailed in the following Examples, which are offered by way of illustration and are not intended to limit the invention in any manner. Standard techniques well known in the art or the techniques specifically described below are utilized.

EXAMPLE 1

Peptide Synthesis

Solid phase peptide synthesis (SPPS) was performed using an Applied Biosystems Model 432A "Synergy" Peptide synthesizer employing Fmoc (9-fluorenylmethoxycarbonyl) strategy. Instrument protocol required 25 $\mu$mol of starting resin and 75 $\mu$mol of subsequent Fmoc-protected amino acids activated by a combination of N-hydroxybenzotriazole (HOBt) and 2-(1-H Benzotriazol-1-yl)-1,1,3,3-tetramethyluroniumhexafluorophosphate (HBTU). Tri-t-butyl DTPA (75 $\mu$mol), prepared internally, was placed in an "amino acid column" at the appropriate location. The Fmoc-protected amino acids were purchased commercially unless otherwise stated; the pre-packaged amino acids were obtained from PE Biosystems while those unavailable in pre-packed cartridges, such as the D amino acids, were supplied by BACHEM or Novabiochem. The arginine mimics were purchased from RSP Amino Acid Analogues. All other peptide synthesis reagents were obtained from PE Biosystems. Cleavage and deprotection were accomplished using 85% TFA/5% thioanisole/5% phenol/5% water. The TFA was supplied by Pierce Chemical while the other cleavage reagents were purchased from Aldrich. The crude peptide was isolated by precipitation with t-butyl methyl ether (Sigma) and purified by reverse phase HPLC using an acetonitrile/water gradient containing 0.1% TFA. Molecular weight determination was accomplished by mass spectrometry operating in the electrospray mode (ESI).

EXAMPLE 2

Competitive Binding Assay

Frozen tissue sections from receptor-positive human tumors were used in a competitive binding assay. Tissue samples were incubated with radioiodinated native neurotensin for 150 minutes at room temperature. Increasing amounts of the cold neurotensin derivatives were then added to generate competitive inhibition curves from which the $IC_{50}$ values were extrapolated.

EXAMPLE 3

Standard Labeling Protocol

All reagents were purchased from Sigma unless otherwise noted. The peptide and $^{111}InCl_3$ in 0.05 N HCl were incubated in a sodium acetate/ascorbic acid buffer for 30 minutes at room temperature. The reaction was diluted with 5% ethanol/95% PBS before using in subsequent in vitro assays.

EXAMPLE 4

In Vitro Serum and Urine Stability Assays

Human serum was purchased from Sigma (H 1388). The labeled peptide was incubated in either human serum or rat urine at 37EC for the specified amount of time. An aliquot was filtered through a 0.45 $\mu$m syringe filter prior to HPLC injection.

EXAMPLE 5

Arginine Mimics

An arginine mimic consists of a glycine moiety connected to a guanidino group with a spacer. The preferred ones have the formula:

CM-$R_3$-$(CA)_n$-$AA_1$-$AA_2$-$AA_3$-$AA_4$-$AA_5$-$AA_6$-OH, wherein
  CM is a chelating moiety or metal binding site wherein the chelating moiety is labeled with a metal isotope selected from $^{99m}Tc$, $^{203}Pb$, $^{67}Ga$, $^{111}In$, $^{97}Ru$, $^{62}Cu$, $^{186}Re$, $^{188}Re$, $^{90}Y$, $^{121}Sn$, $^{161}Tb$, $^{153}Sm$, $^{166}Ho$, $^{105}Rh$, $^{177}Lu$ or a radioactive halogen isotope on the understanding that
  i) if the label is a metal isotope, CM represents a chelating group suitable for the metal and
  ii) if the label is a radioactive halogen isotope, the halogen is attached to an aromatic ring,
  wherein the CM is attached directly or through a spacing group to the peptide, said chelating moiety being attached to the amine through an amide or urea bond or by any other modification which allows attachment of a chelate and which modifications are known to those of skill in the art,
  wherein the chelating group is preferably derived from ethylene diamine tetraacetic acid (EDTA), diethylene triamine pentaacetic acid (DTPA), cyclohexyl 1,2-diamine tetraacetic acid (CDTA), ethyleneglycol-O,O=-bis(2-aminoethyl)-N,N,N',N'-diacetic acid (HBED), triethylene tetraamine hexaacetic acid (TTHA), 1,4,7,10-tetraazacyclododecane-N,N',N'',N'''-tetraacetic acid (DOTA), 1,4,7-triazacyclononane-N,N',N''-triacetic acid (NOTA), 1,4,8,11-tetraazacyclotetradecane-N,N',N'',N'''-tetraacetic acid (TETA) or a compound with a general formula

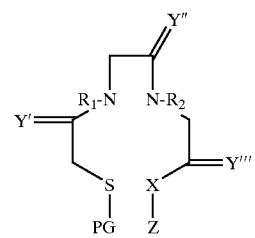

wherein
PG is a sulfur protecting group selected from alkanoyl, arylcarbonyl, arylalkanoyl, acetamidomethyl, tetrahydropyranyl and tetrahydrofuranyl, Y', Y", and Y'" are hydrogen or oxygen with the proviso that at least one of them is an O, $R_1$ and $R_2$ are hydrogen or alkyl ($C_1$–$C_3$), X=NH or S with the proviso that Y'" is hydrogen when X is S, Z is PG if X is S, and Z is hydroxyalkyl, aminoalkyl or carboxyalkyl;

$R_3$ is DLys, DPhe or other D-amino acid, a spacer unit such as Gly-Gly-Gly, Gly-SerGly, Tyr-Glu-Asn, DTyr-Glu-Asn, Phe-Glu-Asn or DPhe-Glu-Asn, or piperidinyl glycine (PipGly), aminomethylcyclohexylalanine (Amcha), other amino acid containing a cycloalkyl ring at the α- or β-position with an amine group or an alkyl amino substituent either externally or as a part of the ring;

CA is a cyclic amino acid selected from Pro, Hyp, 4-oxo-proline [4OPro], pipecolic acid (PipCA), azetidinecarboxylic acid (AzeCA), other amino acid containing a cycloalkyl ring at the α- or β-position with an amine group or an alkyl amino substituent either externally or as a part of the ring;

n=0, 1 or 2;

$AA_1$=an amino acid containing a guanidino group except arginine, wherein the configuration at the α-carbon is either L- or D-, e.g.,

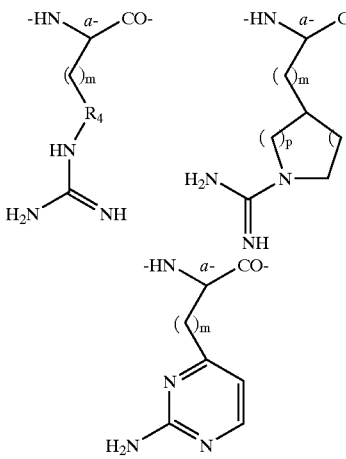

m=0–6;

$R_4$ is a cycloalkyl group ($C_3$–$C_{10}$), phenyl group, aralkyl group, substituted phenyl group or substituted aralkyl group with electron withdrawing or electron donating group with the proviso that the guanidino group is present at a position not occupied by the substituent on the phenyl group;

p=1–7;

q=1–7;

$AA_2$ is arginine, lysine, piperidinylglycine (PipGly), or other amino acid containing a cycloalkyl ring at the α- or β-position with an amine group or alkyl amino substituent either externally or as a part of the ring, wherein the amino acid can have the L- or D-configuration at the α-carbon, or $AA_2$ is an amino acid containing a guanidino group wherein the configuration at the α-carbon is either L- or D-, e.g.,

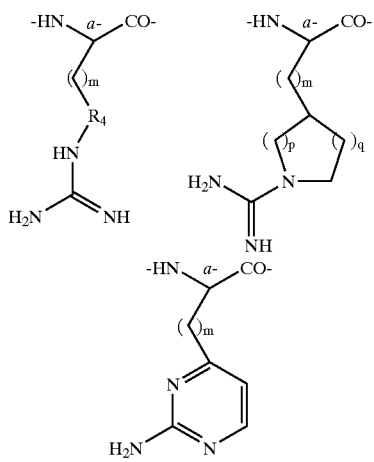

$AA_3$ is a cyclic amino acid selected from Pro, Hyp, 4-oxo-proline [4OPro], pipecolic acid (PipCA), azetidinecarboxylic acid (AzeCA), or other amino acid containing a cycloalkyl ring at the α- or β-position with an amine group or alkyl amino substituent either externally or as a part of the ring, wherein the amino acid can have the L- or D-configuration at the α-carbon;

$AA_4$ is Phe, Tyr, an isomer of Tyr, polyhydroxylated Phe, or other aromatic amino acid, wherein the amino acid can have the L- or D-configuration at the α-carbon;

$AA_5$ is Ile; and $AA_6$ is Leu.

Preferred compounds include compounds I–VII:

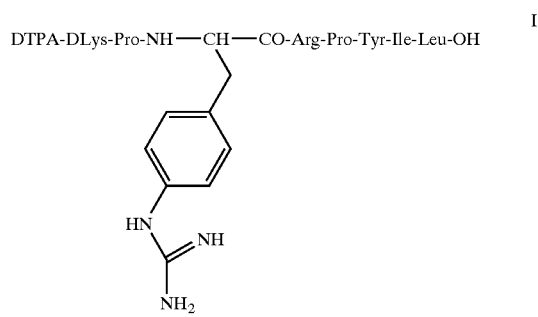

I

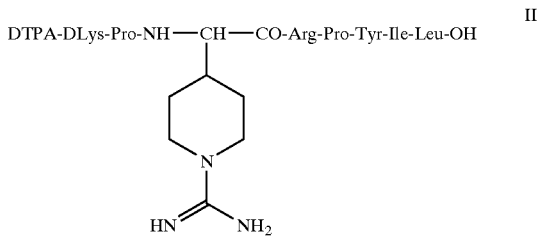

II

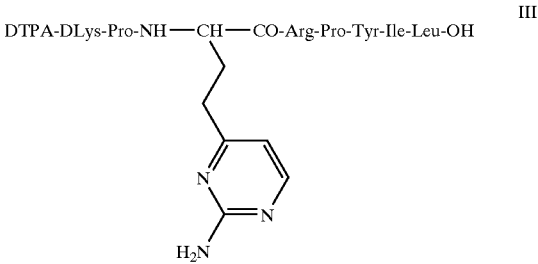

III

-continued

DTPA-DLys-Pro-NH—CH—CO-Arg-Pro-Tyr-Ile-Leu-OH  IV

[structure: CH side chain is ethyl-4-piperidine with N-C(=NH)NH₂ guanidino group]

DTPA-DLys-Pro-NH—CH—CO-Arg-Pro-Tyr-Ile-Leu-OH  V

[structure: CH side chain is pyrrolidine with N-C(=NH)NH₂]

DTPA-DLys-Pro-NH—CH—CO-Arg-Pro-Tyr-Ile-Leu-OH  VI

[structure: CH with pyrrolidine bearing N-C(=NH)NH₂ amidine, NH₂]

DTPA-DLys-Pro-NH—CH—CO-Arg-Pro-Tyr-Ile-Leu-OH  VII

[structure: CH with CH₂-pyrrolidine bearing amidine]

DTPA-DLys-Pro-NH—CH—CO-Arg-Pro-Tyr-Ile-Leu-OH  VIII

[structure: CH with CH₂-pyrrolidin-3-yl bearing N-C(=NH)NH₂]

Substitution of arginine with an arginine mimic or a constrained arginine as shown in compounds I–VIII increases the serum stability of these compounds considerably as shown in Table 1.

TABLE 1

| Compound | $K_d$ | % of compound present at 4 hours | |
|---|---|---|---|
| | | in serum | in urine |
| DTPA-Arg-Arg-Pro-Tyr-Ile-Leu-OH (SEQ ID NO: 3) | 40 | 1.6 | 13.0 |
| Compound I | 8.6 | 14.1 | 1.5 |
| Compound II | 2.7 | 19.5 | 16.6 |
| Compound III | 68 | 4.3 | 6.0 |

As can be seen in Table 1, the presence of constrained arginine increased the serum stability considerably compared to the compound containing the Arg-Arg bond.

Novel neurotensin derivatives were prepared by replacing one or both arginines with the following mimics.

[Arg structure]
Arg

[nArg structure]
nArg

[Phe(4-Gu) structure]
Phe(4-Gu)

[Aba(Apy) structure with aminopyrimidine]
Aba(Apy)

[Ala(Pyra) structure with pyrrolidine-amidine]
Ala(Pyra)

[Gly(PipAm) structure with piperidine-amidine]
Gly(PipAm)

The binding affinities of the neurotensin derivatives with the incorporated Arg mimics are as follows:

TABLE 2

HPLC Evaluation of Serum and Urine Stability at 37EC

| Compound | Prep | Serum, t = 0 | Serum, t = 4 h | Urine, t = 0 | Urine, t = 4 h |
|---|---|---|---|---|---|
| In-111-DTPA-R-R-P-Y-I-L (SEQ ID NO:3) | 97.6%<br>rt = 14.2 m | 92%<br>rt = 14.2 m | 1.6%<br>rt = 14.2 m | 96.7%<br>rt = 14.2 m | 13.0%<br>rt = 14.2 m |
| In-111-DTPA-$_D$K-P-R-F(Gu)-P-Y-I-L | 95.5%<br>rt = 15.1 m | 94%<br>rt = 15.1 m | 16.3%<br>rt = 15.1 m | 90.4%<br>rt = 14.7 m | 0%<br>rt = 14.7 m |
| In-111-DTPA-$_D$K-P-F(Gu)-R-P-Y-I-L | 98.7%<br>rt = 14.6 m | 98.7%<br>rt = 14.6 m | 14.1%<br>rt = 14.6 m | 94.1%<br>rt = 14.6 m | 1.5%<br>rt = 14.6 m |
| In-111-DTPA-$_D$K-P-F(Gu)-F(Gu)-P-Y-I-L | 99.4%<br>rt = 14.6 m | 99.0%<br>rt = 14.6 m | 25.2%<br>rt = 14.6 m | 92.3%<br>rt = 14.6 m | 2.3%<br>rt = 14.6 m |
| In-111-DTPA-$_D$K-P-R-Aba(Apy)-P-Y-I-L | 99.6%<br>rt = 14.8 m | 98.1%<br>rt = 14.8 m | 15.7%<br>rt = 14.8 m | 96.7%<br>rt = 14.8 m | 4.7%<br>rt = 14.8 m |
| In-111-DTPA-$_D$K-P-Aba(Apy)-R-P-Y-J-L | 99.8%<br>rt = 14.8 m | 96.9%<br>rt = 14.8 m | 4.3%<br>rt = 14.8 m | 95.6%<br>rt = 14.8 m | 6.0%<br>rt = 14.8 m |
| In-111-DTPA-$_D$K-P-G(PipAm)-R-P-Y-I-L | 99.3%<br>rt = 13.8 m | Not available | 19.5%<br>rt = 13.8 m | Not available | 16.6%<br>rt = 13.8 m |

EXAMPLE 6

Neurotensin Derivatives Containing Both Arg Mimics and C-Terminus Modifications It was further recognized that there is a secondary site of metabolism between Ile-Leu-OH (AA$_5$-AA$_6$). Hence Ile was replaced by a bulkier side chain to stabilize the bond from further degradation. Compounds were made of the formula CM-R$_3$-(CA)$_n$-AA$_1$-AA$_2$-AA$_3$-AA$_4$-AA$_5$-AA$_6$-OH wherein
- CM is a chelating moiety or metal binding site wherein the chelating moiety is labeled with a metal isotope selected from $^{99m}$Tc, $^{203}$Pb, $^{67}$Ga, $^{111}$In, $^{97}$Ru, $^{188}$Re, $^{90}$Y, $^{121}$Sn, $^{161}$Tb, $^{153}$Sm, $^{166}$Ho, $^{105}$Rh, $^{177}$Lu or a radioactive halogen isotope on the understanding that
  i) if the label is a metal isotope, CM represents a chelating group suitable for the metal and
  ii) if the label is a radioactive halogen isotope, the halogen is attached to an aromatic ring,
  wherein the CM is attached directly or through a spacing group to the peptide, said chelating moiety being attached to the amine through an amide or urea bond or by any other modification which allows attachment of a chelate and which modifications are known to those of skill in the art,
  wherein the chelating group is preferably derived from ethylene diamine tetraacetic acid (EDTA), diethylene triamine pentaacetic acid (DTPA), cyclohexyl 1,2-diamine tetraacetic acid (CDTA), ethyleneglycol-O,O=-bis(2-aminoethyl)-N,N,N',N'-diacetic acid (HBED), triethylene tetraamine hexaacetic acid (TTHA), 1,4,7,10-tetraazacyclododecane-N,N',N",N'''-tetraacetic acid (DOTA), 1,4,7-triazacyclononane-N,N',N"-triacetic acid (NOTA), 1,4,8,11-tetraazacyclotetradecane-N,N',N",N'''-tetraacetic acid (TETA) or a compound with a general formula wherein PG is a sulfur protecting group selected from alkanoyl, arylcarbonyl, arylalkanoyl, acetamidomethyl, tetrahydropyranyl and tetrahydrofuranyl, Y', Y", and Y''' are hydrogen or oxygen with the proviso that at least one of them is an O, R$_1$ and R$_2$ are hydrogen or alkyl (C$_1$–C$_3$), X=NH or S with the proviso that Y''' is hydrogen when X is S, Z is PG if X is S, and Z is hydroxyalkyl, aminoalkyl or carboxyalkyl;

R$_3$ is DLys, DPhe or other D-amino acid, a spacer unit such as Gly-Gly-Gly, Gly-SerGly, Tyr-Glu-Asn, DTyr-Glu-Asn, Phe-Glu-Asn or DPhe-Glu-Asn, or piperidinyl glycine (PipGly), aminomethylcyclohexylalanine (Amcha), other amino acid containing cycloalkyl ring at the α- or β-position with an amine group or an alkyl amino substituent either externally or as a part of the ring;

CA is a cyclic amino acid selected from Pro, Hyp, 4-oxo-proline [4OPro], pipecolic acid (PipCA), azetidinecarboxylic acid (AzeCA), other amino acid containing cycloalkyl ring at the α- or α-position with an amine group or an alkyl amino substituent either externally or as a part of the ring;

n=0, 1 or 2;

AA$_1$ is an amino acid containing a guanidino group except arginine, wherein the configuration at the α-carbon is either L- or D-, e.g., -continued

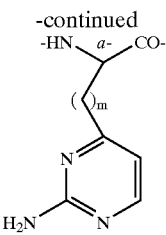

m=0–6;
R_4 is a cycloalkyl group ($C_3$–$C_{10}$), phenyl group, aralkyl group, substituted phenyl group or substituted aralkyl group with electron withdrawing or electron donating group with the proviso that the guanidino group is present at a position not occupied by the substituent on the phenyl group;
p=1–7;
q=1–7;
AA_2 is arginine, lysine, piperidinylglycine (PipGly), or other amino acid containing a cycloalkyl ring at the α- or β-position with an amine group or alkyl amino substituent either externally or as a part of the ring, wherein the amino acid can have the L- or D-configuration at the α-carbon, or AA_2 is an amino acid containing a guanidino group wherein the configuration at the α-carbon is either L- or D-, e.g.,

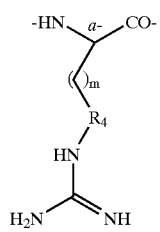 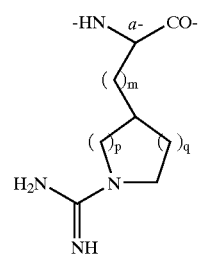

-continued

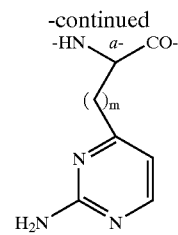

AA_3 is a cyclic amino acid selected from Pro, Hyp, 4-oxo-proline [4OPro], pipecolic acid (PipCA), azefidinecarboxylic acid (AzeCA), or other amino acid containing a cycloalkyl ring at the α- or β-position with an amine group or alkyl amino substituent either externally or as a part of the ring, wherein the amino acid can have the L- or D-configuration at the α-carbon;

AA_4 is Phe, Tyr, an isomer of Tyr, polyhydroxylated Phe, or other aromatic amino acid, wherein the amino acid can have the L- or D-configuration at the α-carbon;

AA_5 is t-butylglycine (tBuGly), 1-aminocyclohexylcarboxylic acid (Achc), cyclohexylglycine (Chg), trimethylsilylalanine, Ile, or other amino acid containing a branched or cyclic hydrocarbon substituent at the side chain at the α- or β-position, wherein the amino acid can have the L- or D-configuration at the α-carbon; and AA_6 is cyclopropylalanine (Cpa), cyclohexylalanine (Cha), t-butylalanine (tBuala), Leu, or other amino acid containing a branched or cyclic hydrocarbon substituent at the side chain at the α- or β-position, wherein the amino acid can have the L- or D-configuration at the α-carbon.

Preferred compounds are:

DTPA-DLys-Pro-NH—CH—CO-Arg-Pro-Tyr-tBuGly-Leu-OH

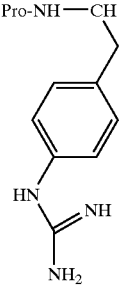

IX

DTPA-DLys-Pro-NH—CH—CO-Arg-Pro-Tyr-tBuGly-Leu-OH

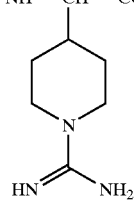

X

-continued

DTPA-NH—CH—CO-Pro-NH—CH—CO-Arg-Pro-Tyr-tBuGly-Leu-OH, XI

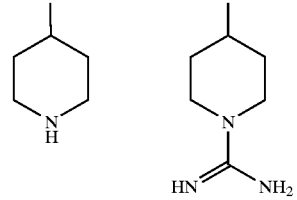

SEQ ID NO: 4

DTPA-NH—CH—CO-Pro-NH—CH—CO-Arg-Pro-Tyr-tBuGly-Leu-OH, XII

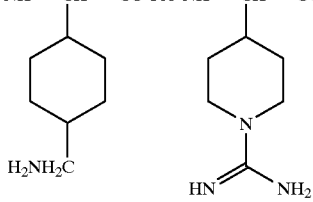

SEQ ID NO: 5

DTPA-DTyr-Glu-Asn-Lys-Pro-NH—CH—CO-Arg-Pro-Tyr-tBuGly-Leu-OH, XIII

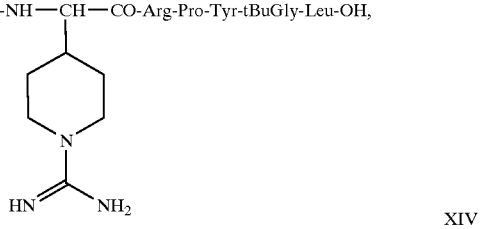

DTPA-DTyr-Glu-Asn-Lys-Pro—NH—CH—CO-Arg-Pro-Tyr-tBuGly-Cha-OH, XIV

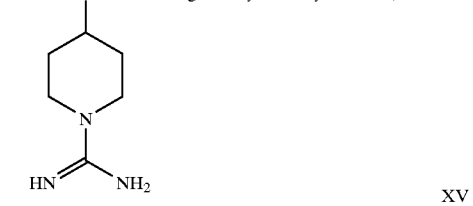

DTPA-DTyr-Glu-Asn-Lys-Pro—NH—CH—CO-Arg-Pro-Tyr-tBuGly-tBuAla-OH, XV

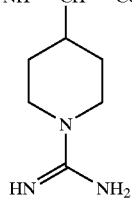

DTPA-DLys-Pro-Gly(PipAm)-Arg-(4-oxo)Pro-Tyr-tBuGly-Leu-OH,
DTPA-DLys-Pro-Gly(PipAm)-Arg-Pro-(2,6diMe)Tyr-tBuGly-Leu-OH,
DTPA-DLys-Pro-Gly(PipAm)-Arg-Pro-mTyr-tBuGly-Leu-OH, wherein mTyr stands for metatyrosine such that the —OH group of the Tyr is in the meta position,
DTPA-DLys-Pro-Gly(PipAm)-PipGly-Pro-Tyr-tBuGly-Leu-OH,
DTPA-DLys-Pro-Gly(PipAm)-Arg-AzeCA-Tyr-tBuGly-Leu-OH,
DTPA-DLys-AzeCA-Gly(PipAm)-Arg-Pro-Tyr-tBuGly-Leu-OH,
DTPA-DLys-Pro-Gly(PipAm)-Arg-Pro-Tyr-Achc-Leu-OH,
DTPA-DLys-Pro-Gly(PipAm)-Arg-Pro-Tyr-tBuGly-Cpa-OH,
DTPA-DLys-Pro-Gly(PipAm)-Arg-Pro-Tyr-tBuGly-Cha-OH,
DTPA-DLys-Pro-Gly(PipAm)-Arg-Pro-Tyr-tBuGly-tBuAla-OH,
DTPA-DLys-Pro-Gly(PipAm)-Arg-PipCA-Tyr-tBuGly-Leu-OH,
DTPA-DLys-Pro-Gly(PipAm)-Arg-DPipCA-Tyr-tBuGly-Leu-OH,
DTPA-DLys-Pro-Gly(PipAm)-Arg-Pro-Tyr-Chg-Leu-OH,
DTPA-DLys-Pro-Gly(PipAm)-Arg-Pro-DTyr-tBuGly-Leu-OH, with compounds XI and XII being the most preferred compounds.

Serum stability of these compounds was considerably increased upon substitution of $AA_5$ with t-butylglycine as shown in Table 3.

TABLE 3

| Sequence | $K_d$ | % of peptide at 4 hours after incubation at 37°C Serum | % of peptide at 4 hours after incubation at 37°C Urine |
|---|---|---|---|
| DTPA-Arg-Arg-Pro-Tyr-Ile-Leu-OH (SEQ ID NO: 3) | 40 | 1.6 | 13.0 |
| DTPA-DLys-Pro-Arg-(4-Gu)Phe-Pro-Tyr-Ile-Leu-OH | 83 | 16.3 | 0 |
| DTPA-DLys-Pro-(4-Gu)Phe-Arg-Pro-Tyr-Ile-Leu-OH (Compound I) | 8.6 | 14.1 | 1.5 |
| DTPA-DLys-Pro-(4-Gu)Phe-(4-Gu)Phe-Pro-Tyr-Ile-Leu-OH | 175 | 25.2 | 2.3 |
| DTPA-DLys-Pro-Arg-Aba(Apy)-Pro-Tyr-Ile-Leu-OH | 1200 | 15.7 | 4.7 |
| DTPA-DLys-Pro-Aba(Apy)-Arg-Pro-Tyr-Ile-Leu-OH | 68 | 4.3 | 6.0 |
| DTPA-DLys-Pro-Aba(Apy)-Aba(Apy)-Pro-Tyr-Ile-Leu-OH | >10000 | ND | ND |
| DTPA-DLys-Pro-(4-Gu)Phe-Mg-Pro-Tyr-tBuGly-Leu-OH (Compound IX) | 12.5 | 72.0 | 51.1 |
| DTPA-DLys-Pro-(4-Gu)Phe-Arg-Pro-Tyr-Leu-($\Psi$-$CH_2$-NH)-Leu-OH | >10000 | 76.2 | 95.7 |
| DTPA-DLys-Pro-Gly(PipAm)-Arg-Pro-Tyr-Ile-Leu-OH (Compound II) | 2.7 | 19.5 | 16.6 |
| DTPA-DLys-Pro-Gly(PipAm)-Arg-Pro-Tyr-tBuGly-Leu-OH (Compound X) | 3.5 | 87.5 | 63.0 |
| DTPA-DLys-Pro-Gly(PipAm)-Arg-(4-oxo)Pro-Tyr-tBuGly-Leu-OH | >1000 | 78.5 | 79.7 |
| DTPA-DLys-Pro-Gly(PipAm)-Arg-Pro-(2,6-diMe)Tyr-tBuGly-Leu-OH | 45 | 96.6 | 99.2 |
| DTPA-DLys-Pro-Gly(PipAm)-Arg-Pro-mTyr-tBuGly-Leu-OH | 300 | 84.4 | 57.8 |
| DTPA-DLys-Pro-Gly(PipAm)-Arg-Pro$^R$-OCO-Tyr-tBuGly-Leu-OH (wherein Pro$^R$-OCO indicates that the bond between the proline and the OCO is a reduced peptide bond) | >10000 | ND | ND |
| DTPA-DLys-Pro-Gly(PipAm)-PipGly-Pro-Tyr-tBuGly-Leu-OH | 140 | 91.6 | 79.7 |
| DTPA-DLys-Pro-Gly(PipAm)-Arg-AzeCA-Tyr-tBuGly-Leu-OH | 740 | 79.2 | 36.5 |
| DTPA-DLys-AzeCA-Gly(PipAm)-Arg-Pro-Tyr-tBuGly-Leu-OH | 24 | 79.5 | 49.8 |
| DTPA-DLys-Pro-Gly(PipAm)-Arg-Pro-Tyr-Achc-Leu-OH | >10000 | 89.9 | 84.9 |
| DTPA-DLys-Pro-Gly(PipAm)-Arg-Pro-Tyr-tBuGly-Cpa-OH | 290 | 88.1 | 73.6 |
| DTPA-DLys-Pro-Gly(PipAm)-Arg-Pro-Tyr-tBuGly-Cha-OH | 12 | 81.2 | 65.9 |
| DTPA-DLys-Pro-Gly(PipAm)-Arg-Pro-Tyr-tBuGly-tBuAla-OH | 7.3 | 89.2 | 72.3 |
| DTPA-DLys-Pro-Gly(PipAm)-Arg-PipCA-Tyr-tBuGly-Leu-OH | >1000 | 69.5 | 45.8 |
| DTPA-DLys-Pro-Gly(PipAm)-Arg-DPipCA-Tyr-tBuGly-Leu-OH | >1000 | 96.2 | 91.9 |
| DTPA-DLys-Pro-Gly(PipAm)-Arg-Pro-Tyr-Chg-Leu-OH | 25 | 75.2 | 7.0 |
| DTPA-DLys-Pro-Gly(PipAm)-Arg-Pro-Tyr-Ile$^R$-OCO-Leu-OH (wherein Ile$^R$-OCO indicates a reduced peptide bond between Ile and OCO) | >1000 | 94.6 | 89.8 |
| DTPA-(Pip)Ala-Pro-Gly(PipAm)-Arg-Pro-Tyr-tBuGly-Leu-OH (SEQ ID NO: 6) (wherein (Pip)Ala represents piperidinyl alanine) | >1000 | 98.9 | 98.3 |
| DTPA-DLys-Pro-Gly(PipAm)-Arg-Pro-DTyr-tBuGly-Leu-OH | 6.4 | 98.9 | 98.3 |
| DTPA-DLys-Pro-Ala(PipAm)-Arg-Pro-Tyr-tBuGly-Leu-OH (where Ala(PipAm) represents (N-amidinopiperidinyl)alanine) | 14 | 96.5 | 89.8 |
| DTPA-DLys-Pro-homoAla(PipAm)-Arg-Pro-Tyr-tBuGly-Leu-OH (wherein homoAla(PipAm) represents (N-amidinopiperidinyl)homoalanine) | 14 | 84.3 | 71.3 |
| DTPA-DLys-Pro-Gly(PipAm)-Arg-Pro-Tyr-tBuGly-Leu-HA (wherein HA indicates that this peptide ends in hydroxamic acid) | 49 | 89.2 | 60.2 |
| DTPA-PipGly-Pro-Gly(PipAm)-Arg-Pro-Tyr-tBuGly-Leu-OH (Compound XI) (SEQ ID NO: 4) | 3.9 | 95.9 | 93.6 |
| DTPA-trans-Cha(4-$CH_2NH_2$)-Pro-Gly(PipAm)-Arg-Pro-Tyr-tBuGly-Leu-OH (Compound XII) (SEQ ID NO: 5) | 5.0 | 94.8 | 89.4 |
| DTPA-DTyr-Glu-Asn-Lys-Pro-Gly(PipAm)-Arg-Pro-Tyr-tBuGly-Leu-OH (Compound XIII) | 4.5 | 94.9 | 86.8 |
| DTPA-DTyr-Glu-Asn-Lys-Pro-Gly(PipAm)-Arg-Pro-Tyr-tBuGly-Cha-OH (Compound XIV) | 4.5 | 93.9 | 81.8 |
| DTPA-DTyr-Glu-Asn-Lys-Pro-Gly(PipAm)-Arg-Pro-Tyr-tBuGly-tBuAla-OH (Compound XV) | 3.5 | 98.9 | 89.8 |

While serum stability was increased by the incorporation of Arg mimics within neurotensin, the HPLC data suggested that the C-terminal portion of the peptide may also undergo degradation (due to the presence of metabolites with slightly shorter retention times). To address this problem, additional derivatives were prepared which retained the Arg mimic that contributed to the lowest $IC_{50}$. The C-terminus was then modified to impart greater enzymatic stability.

| | $IC_{50}$ (nM) |
|---|---|
| DTPA-DLys-Pro-Phe(4-guanyl)-Arg-Pro-Tyr-tBuGly-Leu-OH | 12.5 |
| DTPA-DLys-Pro-Phe(4-guanyl)-Arg-Pro-Tyr-Leu($\Psi$-$CH_2NH$)-Leu-$NH_2$ | >1000 |
| DTPA-DLys-Pro-Gly(PipAm)-Arg-Pro-Tyr-tBuGly-Leu-OH | 3.5 |

TABLE 4

Serum and Urine Stability of Neurotensin Derivatives Modified at the C-Terminus

| Compound | Prep | Serum (t = 4 h) | Urine (t = 4 h) |
|---|---|---|---|
| In-111-DTPA-R-R-P-Y-I-L (SEQ ID NO: 3) | 97.6% rt = 14.2 m | 1.6% rt = 14.2 m | 14.0% rt = 14.2 m |
| In-111-DTPA-DK-P-F(Gu)-R-P-Y-I-L | 98.7% rt = 14.6 m | 14.1% rt = 14.6 m | 1.5% rt = 14.6 m |
| In-111-DTPA-DK-P-G(PipAm)-R-P-Y-I-L | 99.3% rt = 13.8 m | 19.5% rt = 13.8 m | 16.6% rt = 13.8 m |
| In-111-DTPA-DK-P-F(Gu)-R-P-Y-tBuG-L | 99.0% rt = 13.6 | 72.0% rt = 13.6 m | 51.1% rt = 13.6 m |
| In-111-DTPA-DK-P-F(Gu)-R-P-Y-L(Ψ-CH$_2$NH)-L-NH$_2$ | 99.7% rt = 13.3 m | 76.2% rt = 13.3 m | 95.7% rt = 13.3 m |
| In-111-DTPA-DK-P-G(PipAm)-R-P-Y-tBuG-L | 99.2% rt = 13.8 m | 87.5% rt = 13.8 m | 63.0% rt = 13.8 m |

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Aronin N, et al. (1982). *Peptides* 3:637–642.
Granier C, et al. (1982). *Eur. J. Biochem.* 124:117–124.
Kitabgi P, et al. (1985). *Rev. Clin. Basic Pharm.* 5:397–486.
Lee Y C, et al. (1984). *J. Clin. Endocrinol. Metab.* 59:45–50.
Mazella J, et al. (1983) *J. Biol. Chem.* 258:3476–3481.
Reubi J C, et al. (1998). *Gut* 42:546–550.
Tourwe D, et al. (1998). *Belg. Tumor Targeting* 3:41–45.

---

What is claimed is:

1. A peptide of structure CM-$R_3$-$(CA)_n$-$AA_1$-$AA_2$-$AA_3$-$AA_4$-$AA_5$-$AA_6$-OH, wherein said peptide has a selective affinity for neurotensin receptors and wherein CM is a chelating moiety or metal binding site;

$R_3$ is D-lysine, D-phenylalanine, any D-amino acid, glycine-glycine-glycine, Gly-SerGly, Tyr-Glu-Asn, DTyr-Glu-Asn, Phe-Glu-Asn, DPhe-Glu-Asn, piperidinyl glycine, aminomethylcyclohexylalanine, amino acid containing a cycloalkyl ring at the α or β position with an amine group or an alkyl amino substituent either externally or as a part of the ring, or a spacer unit;

CA is a cyclic amino acid selected from the group consisting of proline, hydroxyproline, 4-oxo-proline, pipecolic acid, azetidinecarboxylic acid, and other amino acid containing a cycloalkyl ring at the α- or β-position with an amine group or an alkyl amino substituent either externally or as a part of the ring;

n=0, 1 or 2;

$AA_1$ is an amino acid which comprises a guanidino group and wherein the α-carbon is either L- or D-, with the proviso that $AA_1$ is not arginine;

$AA_2$ is arginine, lysine, piperidinylglycine, or other amino acid containing a cycloalkyl ring at the α- or β-position with an amine group or alkyl amino substituent either externally or as a part of the ring, wherein the amino acid can have the L- or D-configuration at the α-carbon, or $AA_2$ is an amino acid which comprises a guanidino group wherein α-carbon is either L- or D-;

$AA_3$ is a cyclic amino acid selected from proline, hydroxyproline, 4-oxo-proline, pipecolic acid, azetidinecarboxylic acid, or other amino acid containing a cycloalkyl ring at the α- or β-position with an amine group or alkyl amino substituent either externally or as a part of the ring, wherein the amino acid can have the L- or D-configuration at the α-carbon;

$AA_4$ is phenylalanine, tyrosine, an isomer of tyrosine, polyhydroxylated phenylalanine, or other aromatic amino acid, wherein the amino acid can have the L- or D-configuration at the α-carbon;

$AA_5$ is isoleucine; and $AA_6$ is leucine.

2. The peptide of claim 1 wherein $AA_1$ is

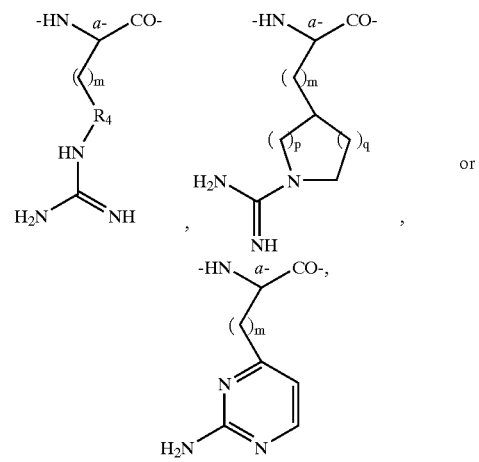

wherein m=0–6;

p=1–7;

q=1–7; and

R₄ is cycloalkyl C₃–C₁₀, phenyl, aralkyl, substituted phenyl or substituted aralkyl comprising an electron withdrawing or electron donating group with the proviso that said guanidino group is at a position different from said electron withdrawing or electron donating group.

3. The peptide of claim 1 wherein said peptide is labeled with a radioisotope.

4. The peptide of claim 3 wherein said label is $^{99m}$Tc, $^{203}$Pb, $^{67}$Ga, $^{111}$In, $^{97}$Ru, $^{62}$Cu, $^{64}$Cu, $^{186}$Re, $^{188}$Re, $^{90}$Y, $^{121}$Sn, $^{161}$Tb, $^{153}$Sm, $^{166}$Ho, $^{105}$Rh, $^{177}$Lu or a radioactive halogen isotope.

5. The peptide of claim 4 wherein if said label is a metal then CM is a chelating group for said metal and if said label is a halogen then said halogen is bound to an aromatic ring.

6. The peptide of claim 1 wherein CM is ethylene diamine tetraacetic acid (EDTA), diethylene triamine pentaacetic acid (DTPA), cyclohexyl 1,2-diamine tetraacetic acid (CDTA), ethyleneglycol-O,O=-bis(2-aminoethyl)-N,N,N', N'-diacetic acid (HBED), triethylene tetraamine hexaacetic acid (TTHA), 1,4,7,10-tetraazacyclododecaneN,N',N'',N'''-tetraacetic acid (DOTA), 1,4,7-triazacyclononane-N,N',N'-triacetic acid (NOTA), 1,4,8,11-tetraazacyclotetradecane-N, N',N'',N'''-tetraacetic acid (TETA) or a compound of formula wherein PG is a sulfur protecting group selected from the group consisting of alkanoyl, arylcarbonyl, arylalkanoyl, acetamidomethyl, tetrahydropyranyl and tetrahydrofuranyl;

Y', Y'', and Y''' are hydrogen or oxygen with the proviso that at least one of them is an O;

R₁ and R₂ are hydrogen or alkyl (C₁–C₃);

X=NH or S with the proviso that Y''' is hydrogen when X is S;

Z is PG if X is S; and

Z is hydroxyalkyl, aminoalkyl or carboxyalkyl.

7. The peptide of claim 1 wherein said peptide

8. A peptide of structure CM-R$_3$-(CA)-$_n$-AA$_1$-AA$_2$-AA$_3$-AA$_4$-AA$_5$-AA$_6$-OH, wherein said peptide has a selective affinity for neurotensin receptors and wherein CM is a chelating moiety or metal binding site;

R$_3$ is D-lysine, D-phenylalanine, any D-amino acid, glycine-glycine-glycine, Gly-SerGly, Tyr-Glu-Asn, DTyr-Glu-Asn, Phe-Glu-Asn, DPhe-Glu-Asn, piperidinyl glycine, aminomethylcyclohexylalanine, other amino acid containing a cycloalkyl ring at the α- or β-position with an amine group or an alkyl amino substituent either externally or as a part of the ring, or a spacer unit;

CA is a cyclic amino acid selected from the group consisting of proline, hydroxyproline, 4-oxo-proline, pipecolic acid, azetidinecarboxylic acid, other amino acid containing a cycloalkyl ring at the α- or β-position with an amine group or an alkyl amino substituent either externally or as a part of the ring;

n=0, 1 or 2;

AA$_1$ is an amino acid which comprises a guanidino group and wherein the α-carbon is either L- or D-, with the proviso that AA, is not arginine;

AA$_2$ is arginine, lysine, piperidinylglycine, or other amino acid containing a cycloalkyl ring at the α- or β-position with an amine group or alkyl amino substituent either externally or as a part of the ring, wherein the amino acid can have the L- or D-configuration at the α-carbon, or AA$_2$ is an amino acid which comprises a guanidino group wherein the α-carbon is either L- or D-;

AA$_3$ is proline, hydroxyproline, 4-oxo-proline, pipecolic acid, azetidinecarboxylic acid, or other amino acid containing a cycloalkyl ring at the α- or β-position with an amine group or alkyl amino substituent either externally or as a part of the ring, wherein the amino acid can have the L- or D-configuration at the α-carbon;

AA$_4$ is phenylalanine, tyrosine, an isomer of tyrosine, polyhydroxylated phenylalanine, or other aromatic amino acid wherein said amino acid can have the L- or D-configuration at the α-carbon;

AA$_5$ is t-butylglycine, 1-aminocyclohexylcarboxylic acid, cyclohexylglycine, trimethylsilylalanine, isoleucine, or other amino acid containing a branched or cyclic hydrocarbon substituent at the side chain at the α- or β-position, wherein the amino acid can have the L- or D-configuration at the α-carbon; and AA$_6$ is cyclopropylalanine, cyclohexylalanine, t-butylalanine, leucine, or other amino acid containing a branched or cyclic hydrocarbon substituent at the side chain at the α- or β-position, wherein the amino acid can have the L- or D-configuration at the α-carbon.

9. The peptide of claim 8 wherein AA$_1$ is

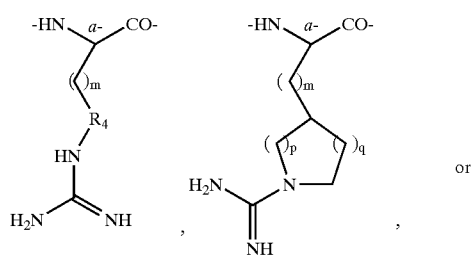

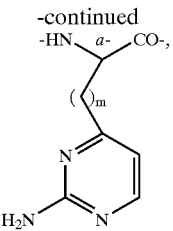

m=0–6;
p=1–7;
q=1–7; and

R$_4$ is cycloalkyl C$_3$–C$_{10}$, phenyl, aralkyl, substituted phenyl or substituted aralkyl comprising an electron withdrawing or electron donating group with the proviso that said guanidino group is at a position different from said electron withdrawing or electron donating group.

10. The peptide of claim 8 wherein said peptide is labeled with a radioisotope.

11. The peptide of claim 10 wherein said label is $^{99m}$Tc, $^{203}$Pb, $^{67}$Ga, $^{111}$In, $^{97}$Ru, $^{62}$Cu, $^{64}$Cu, $^{186}$Re, $^{188}$Re, $^{90}$Y, $^{121}$Sn, $^{61}$T, $^{153}$Sm, $^{166}$Ho, $^{105}$Rh, $^{177}$Lu or a radioactive halogen isotope.

12. The peptide of claim 11 wherein if said label is a metal then CM is a chelating group for said metal and if said label is a halogen then said halogen is bound to an aromatic ring.

13. The peptide of claim 8 wherein CM is ethylene diamine tetraacetic acid (EDTA), diethylene triamine pentaacetic acid (DTPA), cyclohexyl 1,2-diamine tetraacetic acid (CDTA), ethyleneglycol-O,O=-bis(2-aminoethyl)-N,N,N',N'-diacetic acid (HBED), triethylene tetraamine hexaacetice acid (TTHA), 1,4,7,10-tetraazacyclododecane-N,N',N'',N'''-tetraacetic acid (DOTA), 1,4,7-triazacyclononane-N,N',N''-triacetic acid (NOTA), 1,4,8,11-tetraazacyclotetradecane-N,N',N'',N'''-tetraacetic acid (TETA) or a compound of formula

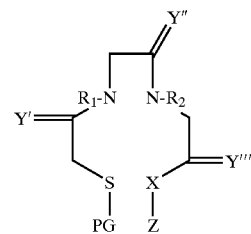

wherein

PG is a sulfur protecting group selected from the group consisting of alkanoyl, arylcarbonyl, arylalkanoyl, acetamidomethyl, tetrahydropyranyl and tetrahydrofuranyl;

Y', Y'', and Y''' are hydrogen or oxygen with the proviso that at least one of them is an 0;

R$_1$ and R$_2$ are hydrogen or alkyl (C$_1$–C$_3$);

X=NH or S with the proviso that Y''' is hydrogen when X is S;

Z is PG if X is S, and Z is hydroxyalkyl, aminoalkyl or carboxyalkyl.

14. The peptide of claim 8 wherein said peptide is DTPA-Arg-Arg-Pro-Tyr-Ile-Leu-OH (SEQ ID NO:3), DTPA-DLys-Pro-Arg-(4-Gu)Phe-Pro-Tyr-Ile-Leu-OH, DTPA-DLys-Pro-(4-Gu)Phe-Arg-Pro-Tyr-Ile-Leu-OH (Compound I),
DTPA-DLys-Pro-(4-Gu)Phe-(4-Gu)Phe-Pro-Tyr-Ile-Leu-OH,
DTPA-DLys-Pro-Arg-Aba(Apy)-Pro-Tyr-Ile-Leu-OH,
DTPA-DLys-Pro-Aba(Apy)-Arg-Pro-Tyr-Ile-Leu-OH,
DTPA-DLys-Pro-Aba(Apy)-Aba(Apy)-Pro-Tyr-Ile-Leu-OH,
DTPA-DLys-Pro-(4-Gu)Phe-Arg-Pro-Tyr-tBuGly-Leu-OH (Compound IX),
DTPA-DLys-Pro-(4-Gu)Phe-Arg-Pro-Tyr-Leu(T-CH$_2$—NH)Leu-OH,
DTPA-DLys-Pro-Gly(PipAm)-Arg-Pro-Tyr-Ile-Leu-OH (Compound II),
DTPA-DLys-Pro-Gly(PipAm)-Arg-Pro-Tyr-tBuGly-Leu-OH (Compound X),
DTPA-DLys-Pro-Gly(PipAm)-Arg-(4-oxo)Pro-Tyr-tBu-Gly-Leu-OH,
DTPA-DLys-Pro-Gly(PipAm)-Arg-Pro-(2,6diMe)Tyr-tBuGly-Leu-OH,
DTPA-DLys-Pro-Gly(PipAm)-Arg-Pro-mTyr-tBuGly-Leu-OH,
DTPA-DLys-Pro-Gly(PipAm)-Arg-Pro$^R$-OCO-Tyr-tBu-Gly-Leu-OH,
DTPA-DLys-Pro-Gly(PipAm)-PipGly-Pro-Tyr-tBuGly-Leu-OH,
DTPA-DLys-Pro-Gly(PipAm)-Arg-AzeCA-Tyr-tBuGly-Leu-OH,
DTPA-DLys-AzeCA-Gly(PipAm)-Arg-Pro-Tyr-tBuGly-Leu-OH,
DTPA-DLys-Pro-Gly(PipAm)-Arg-Pro-Tyr-Achc-Leu-OH,
DTPA-DLys-Pro-Gly(PipAm)-Arg-Pro-Tyr-tBuGly-Cpa-OH,
DTPA-DLys-Pro-Gly(PipAm)-Arg-Pro-Tyr-tBuGly-Cha-OH,
DTPA-DLys-Pro-Gly(PipAm)-Arg-Pro-Tyr-tBuGly-tBuAla-OH,
DTPA-DLys-Pro-Gly(PipAm)-Arg-PipCA-Tyr-tBuGly-Leu-OH,
DTPA-DLys-Pro-Gly(PipAm)-Arg-DPipCA-Tyr-tBu-Gly-Leu-OH,
DTPA-DLys-Pro-Gly(PipAm)-Arg-Pro-Tyr-Chg-Leu-OH,
DTPA-DLys-Pro-Gly(PipAm)-Arg-Pro-Tyr-Ile —OCO-Leu-OH,
DTPA-(Pip)Ala-Pro-Gly(PipAm)-Arg-Pro-Tyr-tBuGly-Leu-OH (SEQ ID NO:6),
DTPA-DLys-Pro-Gly(PipAm)-Arg-Pro-DTyr-tBuGly-Leu-OH,
DTPA-DLys-Pro-Ala(PipAm)-Arg-Pro-Tyr-tBuGly-Leu-OH,
DTPA-DLys-Pro-homoAla(PipAm)-Arg-Pro-Tyr-tBu-Gly-Leu-OH,
DTPA-DLys-Pro-Gly(PipAm)-Arg-Pro-Tyr-tBuGly-Leu-HA,
DTPA-PipGly-Pro-Gly(PipAm)-Arg-Pro-Tyr-tBuGly-Leu-OH (Compound XI) (SEQ ID NO:4),
DTPA-trans-Cha(4-CH$_2$NH$_2$)-Pro-Gly(PipAm)-Arg-Pro-Tyr-tBuGly-Leu-OH
(Compound XII) (SEQ ID NO:5),
DTPA-DTyr-Glu-Asn-Lys-Pro-Gly(PipAm)-Arg-Pro-Tyr-tBuGly-Leu-OH (Compound XIII),
DTPA-DTyr-Glu-Asn-Lys-Pro-Gly(PipAm)-Arg-Pro-Tyr-tBuGly-Cha-OH (Compound XIV), or
DTPA-DTyr-Glu-Asn-Lys-Pro-Gly(PipAm)-Arg-Pro-Tyr-tBuGly-tBuAla-OH (Compound XV).

* * * * *